US007658850B2

(12) United States Patent
Hrsak et al.

(10) Patent No.: US 7,658,850 B2
(45) Date of Patent: Feb. 9, 2010

(54) MIXED BACTERIAL CULTURE FOR ATRAZINE DEGRADATION

(75) Inventors: Dubravka Hrsak, Zagreb (HR); Maja Havriluk, Sesvete (HR)

(73) Assignee: Rudjer Boskovic Institute, Zagreb (HR)

( * ) Notice: Subject to any disclaimer, the term of this patent is extended or adjusted under 35 U.S.C. 154(b) by 0 days.

(21) Appl. No.: 12/194,995

(22) Filed: Aug. 20, 2008

(65) Prior Publication Data

US 2009/0026135 A1  Jan. 29, 2009

Related U.S. Application Data

(63) Continuation of application No. PCT/HR2007/000002, filed on Jan. 22, 2007.

(30) Foreign Application Priority Data

Feb. 20, 2006  (HR)  ............... P 060076 A

(51) Int. Cl.
   *C02F 3/00*  (2006.01)
(52) U.S. Cl. ............... 210/611; 210/903; 435/262.5
(58) Field of Classification Search ............ 210/611, 210/903; 435/262.5
   See application file for complete search history.

(56) References Cited

U.S. PATENT DOCUMENTS

| 5,429,949 | A | 7/1995 | Radosevich et al. |
| 5,508,193 | A | 4/1996 | Mandelbaum et al. |
| 2003/0170879 | A1* | 9/2003 | McTavish ............... 435/262.5 |
| 2004/0208706 | A1* | 10/2004 | Kukor et al. ............ 405/128.75 |
| 2006/0257890 | A1* | 11/2006 | Minshull et al. ............... 435/6 |
| 2007/0101461 | A1* | 5/2007 | Van Der Lelie et al. ..... 800/295 |

OTHER PUBLICATIONS

Behki, Ram M, et al "Degradation of Atrazine, propazine, and Simazine by Rhodococcus Strain B-30" J. Agric Food Chem., pp. 1237-1241, 1994.

Martinez, Better, et al, "Complete Nucleotide Sequence and Organization of the Atrazine Catabolic Plasmid pADP-1 from Pseudomonas sp. Strain ADP" Journal of Bacteriology, pp. 5684-5697, Oct. 2001.

Strong, Lisa C., et al "Arthrobacter aurescens TC1, Metabolizes Diverse s-Trazine Ring Compounds", Applied and Enviromental Microbiology, pp. 5973-5980, Dec. 2002.

Sparling, Graham, et al, "Atrazine miseralisation in New Zealand topsoils and subsoils: influence of edaphic factors and numbers of atrazine-degrading microbes", Australian Journal of Soil Research, pp. 557-570, 1998.

(Continued)

*Primary Examiner*—Chester T Barry
(74) *Attorney, Agent, or Firm*—St. Onge Steward Johnston & Reens LLC

(57) ABSTRACT

The present invention provides a mixed bacterial culture, designated as the culture Atz Mix 1, which degrades atrazine at various temperatures (10° C. to 30° C.) in a wide range of atrazine concentrations (several ppb to ten thousand ppm), without formation of toxic metabolites. Atz Mix 1 is a stable mixed culture and includes catabolic genes trzN, atzB, atzC coding the enzymes for the degradation of atrazine to cyanuric acid, and the gene trzD coding the enzymes for subsequent opening of s-triazine ring. The invention further includes a microbiological method of degrading atrazine and other s-triazine compounds for remediation of atrazine-contaminated soils, even those rich in nitrogen, as well as for accelerating the process of atrazine mineralization in waste waters containing high concentrations of s-triazine compounds.

16 Claims, 5 Drawing Sheets

OTHER PUBLICATIONS de Souza, Mervyn L., "Atrazine Chlorohydrolase from Pseudomonas sp. Straid ADP: Gene Sequence, Enzyme Purification and Protein Characterization" Journal of Bacteriology, pp. 4894-4900, Aug. 1996.

Sadowsky, Michael J., et al, "AtzC is a New Member of the Amidohydrolase Protein Superfamily and Is Homologous to Other Atrazine-Metabolizing Enzymes" Journal of Bacteriology, pgs. 152-158, Jan. 1998.

Topp, Edward, et al, "Characterization of an Atrazine-Degrading Pseudaminobacter sp. Isolated from Canadian and French Agricultural Soils" Applied and Enviromental Microbiology, pp. 2773-2782, Jul. 2000.

Stipicevic, Sanja, et al, "Comparison of gas and high performace liquid chromatography with selective detection for determination of triazine herbicides and their degradation products extracted ultrasonically from soil" Journal of Separation Science, pp. 1237-1246, 2003.

Bouquard, Corinne, et al, "Dechlorination of Atrazine by Rhizobium sp. Isolate", Applied and Environnental Microbiology, pp. 862-866, Mar. 1997.

Radosevich, Mark, et al, "Degradation and Mineralization of Atrazine by a Soil Bacterial Isolate" Applied and Enviromental Microbiology, pp. 297-302, Jan. 1995.

Behki, Ram M., et al "Degradation of Atrazine by Pseudomonas: N-Dealkylation and Dehalogenation of Atrazine and Its Metabolites" J. Agric. Food Chem, pp. 746-749, 1986.

Hrsak, D., et al, "Enrichment of linear alkylbenzenesuplhonate (LAS) degrading bacteria in continuous culture" Journal of Applied Bacteriology, pp. 413-422, 1982.

Gebendinger, N., et al, Inhibition of atrazne degradation by cyanazine and exogenous nitrogen in bacterial isolate M91-3, Appl Microbiol Biotechnol, pp. 375-381, 1999.

International Preliminary Report on Patentability, PCT/HR2007/000002, Feb. 29, 2008, 7 pages.

Rousseaux, Sandrine, et al, "Isolation and characterisation of new Gram-negative and Gram-positive atrazine degrading bacteria from different French soils" FEMS Microbiology, pp. 211-222, 2001.

Mandelbaum, Ralphi T., et al, "Isolation and Characterization of a Pseudomonas sp. That Mineralizes the s-Triazine Herbicide Atrazine" Applied and Enviromental Microbiology, pp. 1451-1457, Apr. 1995.

International Search Report, PCT/HR2007/000002, Jun. 22, 2007, 2 pages.

Kontchou, Clotaire Yanze, et al, "Mineralization of the Herbicide Atrazine in Soil Inoculated with a Pseudomonas Strain" J. Agric. Food Chem., pp. 2291-2294, 1995.

Ralebitso, T. Komang, et al "Microbial aspects of atrazine degradation in natural enviroments" Biodegeneration, pp. 11-19, 2002.

Garcia-Gonzales, Vicente, et al, "Regulation of the Pseudomonas sp. Strain Adp Cyanuric Acid Degradation Operon" Journal of Bacteriology, pgs. 155-167, Jan. 2005.

Smith D et al: "Cooperative catabolic pathways within an atrazine-degrading enrichment culture isolated from soil" Fems Microbiology Ecology, Elsevier, NL, vol. 53, No. 2, Jul. 1, 2005 (Jul. 1, 2005), pp. 265-273, XP004945377 ISSN: 0168-6496 abstract; figures 3,4 paragraph [02.2].

Stucki G et al: "Microbial atrazine mineralisation under carbon limited and denitrifying conditions" Water Research, Elsevier, Amsterdam, NL, vol. 29, No. 1, Jan. 1995 (Jan. 1995), pp. 291-296, XP004035522 ISSN: 0043-1354 abstract.

Boundy-Mills, Kyria L., et al, "The atzB Gene of Pseudomonas sp. Strain ADP Encodes the Second Enzyme of a Novel Atrazine Degradation Pathway", Applied and Enviromental Microbiology, pp. 916-923, Mar. 1997.

Written Opinion of the International Searching Authority, PCT/HR2007/000002, Jun. 22, 2007, 6 pages.

Udikovic, et al., "Enrichment and Characterization of Atrazine Degrading Bacterial Communites"; Food Technol. Biotechnol. 41(3) 211-217; 2003; 7 pages.

\* cited by examiner

MIXED BACTERIAL CULTURE FOR ATRAZINE DEGRADATION

CROSS-REFERENCE TO RELATED APPLICATIONS

The present application is a continuation of pending International patent application PCT/HR2007/000002, filed Jan. 22, 2007, which designates the United States and claims priority from Croatian patent application no. P060076A, filed Feb. 20, 2006, the content of which is incorporated herein by reference.

FIELD OF THE INVENTION

The present invention relates to the microbiological method for degradation of atrazine and other s-triazine compounds using a mixed bacterial culture of specific growth and catabolic characteristics originating from s-triazine contaminated soil.

BACKGROUND OF THE INVENTION

Atrazine (6-chloro-N-ethyl-Nisopropyl-[1,3,5]triazine-2,4-diamine) is an s-triazine herbicide used for broadleaf weed control not only in agricultural land but much wider. The widespread use of atrazine over 30 years and relatively high mobility in soil has resulted in its increasingly frequent detection in surface waters and ground water at the concentrations exceeding the maximum level allowed (3 ppb in the USA and 1-2 ppb in Europe). This fact and the increasing concern regarding its toxicological and ecotoxicological properties have stimulated the investigations of atrazine biodegradability with the aim to develop microbiological methods for accelerating the biodegradation processes at atrazine-polluted sites.

Numerous papers have been published so far dealing with the isolation of microbial cultures from atrazine contaminated soils which showed the activity in the transformation or complete atrazine degradation to inorganic compounds (Behki R M and Khan S U 1986 J. Agric. Food Chem. 34: 746-749; Behki R M and Khan S U 1994 J. Agric. Food Chem. 42: 1237-1241; Radosevich M, Hao Y-L, Traina S J and Tuovinen O H 1995 Appl. Environ. Microbiol. 61: 297-302; Mandelbaum R T, Allan B H and Wackett L P 1995 Appl. Environ. Microbiol. 61: 1451-1457; Yanze-Kontchou C and Gschwind N 1995 J. Agric. Food Chem. 43: 2291-2294; Bouquard C, Ouazzani J, Prom J C, Michel-Briand Y & Plesiat P 1997 Appl. Environ. Microbiol. 63: 862-866; Sparling G, Dragten R, Aislabie J and Fraser R 1998 Aus. J. Soil Res. 36: 557-570; Topp E, Zhu H, Nour S M, Houot S, Lewis M and Cuppels D 2000 Appl. Environ. Microbiol. 66: 2773-2782; Martinez B, Tomkins J, Wackett L P, Wing R and Sadowsky M J 2001 J. Bacteriology 19: 5684-5697; Ralebitso T K, Senior E and van Verseveld H W 2002 Biodegradation 13: 11-19).

From the investigated atrazine-degrading cultures, either the monocultures or the mixed cultures, Gram-negative rod-shaped bacteria are reported to be the most active. However, there is an increasing number of reports about some Gram-positive bacteria (particularly those belonging to the genera *Nocardioides* and *Arthrobacter*) which are capable of degrading atrazine and other s-triazine compounds and express the capability to grow in mineral medium containing these substances as carbon and nitrogen sources. (Strong L C, Rosendahl C, Johnson G, Sadowsky M J and Wackett L P 2002 Appl. Environ. Microbiol. 68: 5973-5980).

From the pure cultures, *Pseudomonas* sp. strain ADP has been to date the most investigated bacterial strain. This strain is the reference strain of extensively investigated atrazine catabolism under aerobic and anaerobic conditions, with determined sequences of catabolic genes coding the transformation of atrazine to cyanuric acid (atzA—de Souza M L, Sadowsky M J and Wackett L P 1996 J. Bacteriol. 178: 4894-4900; atzB—Boundy-Mills K, de Souza M L, Mandelbaum R M, Wackett L P and Sadowsky M J 1997 Appl. Environ. Microbiol. 63: 916-923 and atzC—Sadowsky M J, Tong Z, de Souza M L and Wackett L P 1998 J. Bacteriology 180; 152-158) as well as the sequences of further three genes (atzDEF), coding the subsequent degradation of cyanuric acid to carbon dioxide, ammonium ions and chloride ions (Garcia-Gonzalez V, Govantes F, Perrua O and Santero E 2005 J. Bacteriol. 187: 155-167).

In the U.S. Pat. No. 5,508,193 the method for isolation of *Pseudomonas* sp. strain ADP is described, as well as the conditions for its optimum growth and atrazine mineralization activity. The bacterium is indicated to express catabolic activity at relatively low atrazine concentrations (200 ppb) which are characteristic for minor pollutions, as well as at high atrazine concentrations (2000 ppb), such as those typically occurring in spill sites (run-off water from intensive agriculture, sites of herbicide disposal and agricultural chemical dealership sites) or in technological waste waters from atrazine and other manufacturing plants which contain s-triazine compounds. *Pseudomonas* ADP exhibits sustained growth in mineral medium containing 0.4 mM of atrazine as the sole nitrogen source and 15 mM of suitable carbon source (citrate or succinate). Under these conditions, i.e. under nitrogen limitation (molar ratio of carbon and nitrogen, C/N=45), *Pseudomonas* ADP exhibits maximum catabolic efficiency whereas in the presence of an additional nitrogen source (ammonium nitrate, ammonium phosphate) atrazine degradation is highly suppressed. Considering that most soils are not nitrogen-limited; in fact they are more or less rich in organic and inorganic nitrogen depending on the fertilization modes, and considering that manufacturing waste waters contain various nitrogen compounds, the use of *Pseudomonas* ADP as a bioaugmentation agent for accelerating atrazine mineralization processes and for remediation of contaminated sites frequently does not provide the expected results.

In the U.S. Pat. No. 5,429,949 the isolation and catabolic activity of the Gram-negative bacterium M91-3, characterized as *Ralstonia basilensis* M91-3 (Gebendinger N and Radosevich M 1999 Appl. Microbiol. Biotechnol. 51: 375-381) is described. Similar to *Pseudomonas* ADP, M91-3 grows in the presence of atrazine as the sole nitrogen source, and under the optimum conditions (C/N>30) degrades atrazine to yield ultimate products $CO_2$ and $NH_4^+$. Investigations were performed in aqueous medium at an atrazine concentration of 0.1 mM (approximately 21.5 mg $l^{-1}$) with the addition of glucose (2.2-5.5 mM) as a carbon source. Furthermore, like in the case with *Pseudomonas* ADP, atrazine mineralization by M91-3 has been suppressed in the presence of additional source of nitrogen, either of organic or inorganic origin.

The influence of nitrogen compounds on the regulation of atrazine catabolic pathway has been in focus of numerous studies (Garcia-Gonzalez V, Govantes F, Perrua O and Santero E 2005 J. Bacterid. 187: 155-167) and nitrogen amendments have been shown to have a negative effect on atrazine degradation by most of the known atrazine-degrading bacteria. Thus, nitrogen control of atrazine catabolism may substantially limit the potential of catabolically active bacteria to be efficiently used for atrazine degradation in agricultural soils rich in organic or inorganic nitrogen due to routine fertilization. The attempt to use bacterial mutants with regulated atrazine catabolism, i.e. by overriding the nitrogen control, as bioaugmentation agents for remediation of nitrogen-rich atrazine-contaminated soils met also with limited success due to the embargo on introducing genetically modified microorganisms in the environment, which is in force in most of the countries. There has nither been reported about the commercial application of catabolically active individual or mixed bacterial cultures for treatment of waste waters containing high concentrations of this herbicide.

To summarize, although the microorganisms, bacteria in particular, have been recognized as very efficient biological agents for the transformation of atrazine and other s-triazine compounds, microbiological methods provided so far for the removal of those compounds from natural environment (i.e. for remediation of contaminated sites) are not commercially viable. Accordingly, there is still a need for the development of microbiological methods in which catabolic potential of bacteria will be exploited to rapidly and completely degrade atrazine under varying, often very specific environmental conditions.

SUMMARY OF THE INVENTION

The present invention provides a mixed bacterial culture, designated as the culture Atz Mix 1, which originates from the soil exposed to long-term contamination with atrazine and other s-triazine compounds. The culture Atz Mix 1 degrades atrazine at various temperatures (10° C. to 30° C.) in a wide range of atrazine concentrations (several ppb to ten thousand ppm), without formation of toxic metabolites and leading to the complete atrazine degradation (mineralization). Atz Mix 1 is a stable mixed culture consisting of at least four members of different morphological, physiological and catabolic properties. Molecular characterization of the culture Atz Mix 1 showed the presence of catabolic genes trzN, atzB, atzC coding the enzymes for the degradation of atrazine to cyanuric acid and the gene trzD coding the enzymes for subsequent opening of s-triazine ring whereas high degree of mineralization of ring labelled [$^{14}$C] atrazine (approximately 80%) confirmed that the degradation proceeded to yield $CO_2$ and $NH_4^+$. The microbiological method of degrading atrazine and other s-triazine compounds, which is part of the present invention, is advantageous over the so far described methods using individual bacterial cultures. This is primarily due to the specific growth and catabolic characteristics of the mixed culture Atz Mix 1 used as a biological agent, i.e. due to its capability to express sustained growth and atrazine-degrading efficiency under the conditions similar to those occurring in atrazine-contaminated environment (e.g. varying temperatures, low C/N ratio, presence of preferential nitrogen source, high atrazine concentrations). Furthermore, it should be emphasized that the inhibition of atrazine degradation in the presence of readily accessible nitrogen sources observed with majority of the so far described individual bacterial strains was not recorded with the culture Atz Mix 1. Accordingly, it can be expected that the microbiological method of the present invention will be suitable for remediation of atrazine-contaminated soils, even those rich in nitrogen, as well as for accelerating the process of atrazine mineralization in waste waters containing high concentrations of s-triazine compounds.

BRIEF DESCRIPTION OF THE DRAWINGS

FIG. 4B C/N=10.5; FIG. 4C C/N=2.5 and FIG. 4D CTN=1.8).

DETAILED DESCRIPTION OF THE INVENTION

Figure 1:
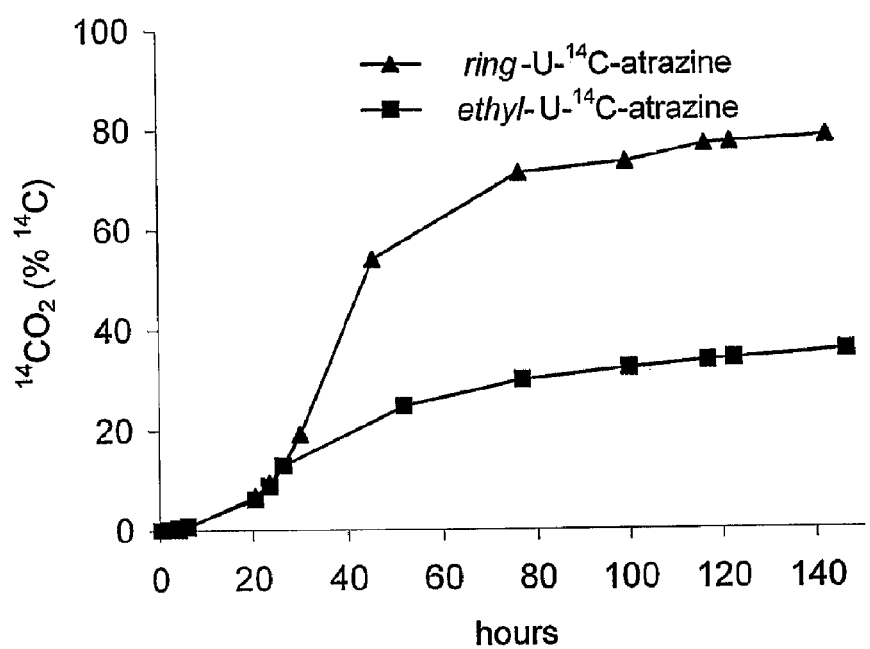
FIG. 1. Atrazine mineralization activity of the culture Atz Mix 1 as determined by radiorespirometric method using ring labelled [$^{14}$C]-atrazine (-▲-) and ethyl-chain labelled [$^{14}$C]-atrazine (-■-).

The present invention provides a mixed bacterial culture designated as Atz Mix 1 that originates from natural environment (soil contaminated with s-triazine compounds) and expresses capability of degrading atrazine and other s-triazine compounds, such as: simazine (6-chloro-N,N'-diethyl-[1, 3,5]triazine-2,4-diamine), propazine (6-chloro-N,N'-diisopropyl-[1,3,5]triazine-2,4-diamine), terbutilazine (6-chloro-N-tert-butyl-N'-ethyl-[1,3,5]triazine-2,4-diamine), deethylatrazine (6-chloro-N-isopropyl-[1,3,5]triazine-2,4-diamine), deisopro-pylatrazine (6-chloro-N-ethyl-[1,3,5]triazine~2,4-diamine), hydroxyatrazine (6-hydroxy-N-ethyl-N'-isopropyl-[1,3,5]triazine-2,4-diamine), hydroxydeisopropylatrazine (6-hydroxy-N-ethyl-[1, 3,5]triazine-2,4-diamine), hydroxy deethylatrazine (6-hydroxy-N-isopropyl-[1, 3,5]triazine-2,4-diamine), hydroxy deethyldeisopropylatrazine (6-hydroxy-[1,3,5]triazine-2,4-diamine) and cyanuric acid (2,4,6-trihydroxy-1,3,5-triazine).

The present invention also provides microbiological methods for degradation of atrazine and other s-triazine compounds which are based on specific catabolic and other characteristics of the culture Atz Mix 1. Until this invention, no other mixed or pure bacterial cultures have been reported to degrade atrazine as rapidly or as completely under the conditions that are similar to those usually occurring in pesticide-contaminated soils (carbon limitation, presence of preferential nitrogen source, low C/N ratio, low temperature, high atrazine concentrations). Complementary catabolic activity of the culture members provides for the complete degradation (mineralization) of atrazine whereas metabolic versatility and mutual interactions between the culture members can contribute towards better adaptation of the mixed culture Atz Mix 1 to varying environmental conditions and the survival of catabolically active bacteria under the conditions that are not favourable for their growth and catabolic activities.

Culture Atz Mix 1

Mixed culture of the present invention has been deposited in the National Collection of Agricultural and Industrial Microorganisms, Budapest, Hungary under the number NCAIM (P) B 001329 2005-12-09. The culture Atz Mix 1 has been enriched from soil exposed to long-term contamination with s-triazine compounds by continuous cultivation in mineral medium containing atrazine as the sole carbon and nitrogen source. The composition of atrazine mineral medium and the conditions of continuous cultivation are described in Example 1.

Mixed culture Atz Mix 1 shows sustained growth and atrazine-degrading activity during cultivation under different conditions (e.g. with or without the supplemental carbon source, at various atrazine concentrations and various temperatures). Plate count examinations during atrazine degradation suggest that the structure of the mixed culture varies depending on the conditions; however, most frequently four morphologically different colony types are present. Further characterization of the mixed culture Atz Mix 1 shows that atrazine mineralization is a result of complementary catabolic activity of the culture members, some of which degrade atrazine to cyanuric acid (identified to belong to the genus *Arthrobacter*) and some other members continue the degradation of cyanuric acid to yield $CO_2$ and $NH_4^+$.

Culture Atz Mix 1 expresses atrazine-degrading activity at temperatures ranging from 10° C. to 30° C., i.e. under the conditions that are not always favorable for its growth. The fastest culture growth and atrazine degradation rate are recorded at the temperature of 30° C.; however, although the growth rate is significantly reduced at lower temperatures, such as those usually occurring in natural environment, the culture Atz Mix 1 retains its significant specific degradation activity even at a temperature of 10° C. The experiments which demonstrate the effect of temperature on the growth and catabolic activity of the culture Atz Mix 1 are presented in Example 2 whereas the results of growth kinetics and atrazine degradation experiments at different initial atrazine concentrations (different carbon and nitrogen ratios) are presented in Example 3, The results of the kinetic experiments showed that despite nearly equal growth rate of the culture Atz Mix 1 at the initial atrazine concentrations of 30 mg $l^{-1}$ and 100 mg $l^{-1}$ (molar ratios of carbon and nitrogen, C/N=31.1 and C/N=10.5) the rate of atrazine degradation was higher at the higher atrazine concentration. Furthermore, the culture Atz Mix 1 expresses comparable degradation capacity (e.g. the maximum specific rate of atrazine degradation in the range of 1.4-1.8 mM per hour per gram of biomass) under the conditions when atrazine concentration is increased to 1000 mg $l^{-1}$ and 5000 mg $l^{-1}$ without increasing carbon source (C/N=2.5 and C/N=1.8) and tolerates high atrazine concentrations (up to 10 g $l^{-1}$). The results of the kinetic experiments also showed that atrazine degradation was not inhibited by the presence of additional nitrogen sources, such as urea, ammonium sulphate or potassium nitrate. Based on these growth and catabolic characteristics it can be expected that the mixed culture of the present invention will be more efficient in the degradation of atrazine and other s-triazine compounds than atrazine-degrading bacterial cultures described so far, particularly in atrazine-contaminated environment when a preferred nitrogen source is present (e.g. nitrogen-fertilized soils) as well as at the sites of very large pollution (e.g. spill sites) and in manufacturing waste water containing high atrazine concentrations.

It can also be assumed that specific metabolic, nutritional and other complex interactions between culture members may induce the changes in mixed culture composition. For this reason the present invention includes all culture variants that have substantially the same catabolic and other identifying characteristics of the culture Atz Mix 1.

Methods for Degradation of Atrazine and Other s-Triazine Compounds

Microbiological method of the present invention provides for the degradation of s-triazine compounds, i.e. for accelerating biotransformation of these compounds in contaminated environment (soil, ground water, surface waters, etc.). The method also provides for the treatment of agrochemical and other technological waste waters that contain s-triazine compounds. Based on the catabolic activity of the mixed culture Atz Mix 1 of the present invention, the method provides for the degradation of s-triazine compounds, preferably atrazine, in contaminated environments, at the sites of minor pollution (100-200 ppb) and the sites of very large pollution (1000-5000 ppm), the latter referring most often to the spills as well as to the irregular handling and storage of these compounds. Depending on the medium and the conditions under which the contaminants are present in the environment, this invention provides for the use of culture Atz Mix 1 as a liquid culture or as an immobilized culture on the adequate carrier (e.g. granulated activated carbon or other solid supports for bacterial attachment).

The method of the present invention involves batch cultivation of the culture Atz Mix 1 in the medium containing the corresponding mineral salts (e.g. $KH_2PO_4$, $K_2HPO_4$, NaCl, $MgSO_4$, $ZnSO_4$, $FeSO_4$, $MnSO_4$, $CUSO_4$), source of vitamins and specific nutrients (e.g. yeast extract), suitable carbon source (e.g. citrate, glucose, succinate) and an amount of atrazine to give a C/N ratio of approximately 30:1. Catabolic activity of the mixed culture of the present invention, expressed as a specific rate of atrazine degradation, is approximately 2.5 mM per hour per gram of biomass dry weight (mM $g^{-1}l^{-1}$). To achieve the best possible effectiveness of the method of this invention, i.e. the most rapid and substantial degradation of s-triazine compounds at the contaminated site (the complete mineralization of these compounds), it is recommended to use the amount of the culture biomass that ensures the atrazine degradation rate of 2.5 mM $g^{-1}l^{-1}$.

EXAMPLE 1

Culturing and Characterization of the Mixed Bacterial Culture

The culture Atz Mix 1 was enriched from the soil collected within an agricultural factory area that was exposed to persistent contamination with atrazine and other s-triazine compounds for more than twenty years. Enrichment of the culture was performed during 2-month cultivation in a continuous-flow unit with the inflow of mineral salts medium containing atrazine as the sole carbon and nitrogen source (dilution rate, D=0.1 $h^{-1}$) at room temperature. The description of the continuous-flow unit is given in Hrsak D, Bosnjak M, and Johanides V 1982 J, Appl. Bacteriology 53: 413-422. Atrazine medium (AMS) consisted of mineral salts: (g $l^{-1}$) $K_2HPO_4$ 1.6; $KH_2PO_4$ 0.4; $MgSO_4\times7$ $H_2O$ 0.2; NaCl 0.1; $CaCl_2\times6H_2O$ 0.04 with the addition of atrazine (25 mg $l^{-1}$), salt stock solution (20 ml $l^{-1}$) and vitamin stock solution (10 ml $l^{-1}$). The salt stock solution contained: (g $l^{-1}$) EDTA 2.5; $ZnSO_4 \times 7H_2O$ 11.1; $FeSO_4$ 5.0; $MnSO_4 \times 7H_2O$ 1.54; $CuSO_4 \times 5H_2O$ 0.4; $Co(NO_3)_2 \times 6H_2O$ 0.25 and $Na_2B_4O_7 \times 10H_2O$ 0.18) and the vitamin stock solution contained: (mg $l^{-1}$) thiamine HCl 5; biotine 2; folic acid 2; nicotinamide 10 and pyridoxine HCL 10). Brief description of the procedure: continuous-flow unit was filled with soil filtrate prepared in phosphate buffer of pH 7.0 (100 g of soil was added to 1 liter of phosphate buffer, mixed for 20 min, allowed to settle and filtered through coarse filter paper), followed by dosage of AMS medium. After 2 month enrichment, the content of the unit was centrifuged (6000 g, 10 min.), biomass was resuspended in phosphate buffer and stored in the refrigerator at $-20°$ C. in small aliquots (10 ml).

In last 2 weeks of the enrichment, residual concentration of atrazine was monitored in the effluent by high performance liquid chromatography (HPLC). The structure of the mixed culture was monitored as well by spreading appropriate culture dilutions onto the solid AMS medium containing atrazine (500 mg $l^{-1}$) and sodium citrate (1 g $l^{-1}$). The HPLC method used and chromatographic conditions are described in Stipicevic S, Fingler S, Zupancic-Kralj L and Drevenkar V 2003 J. Sep. Sci. 26: 1237-1246; here is only noted that the analyses were performed using a system Varian ProStar 230 SDM, equipped with a Varian ProStar 330 UV-detector with a series of photodiodes (UV-DAD) (Varian, Walnut Creek, Calif., USA), and a chromatographic column ODS Hypersil, 250 mm×4.6 mm (particle-size 5 μm) with a guard column Hypersil ODS chromatographic (10×4 mm, 5 μm), Thermo Hypersil-Keystone, Bellefonte, Pa., USA. Identification of atrazine and other s-triazine compounds as well as degradation intermediates was made according to the retention times and UV-spectra of the authentic standards.

HPLC analysis of the culture samples from the continuous-flow unit confirmed the complete disappearance of atrazine while the analysis of the colonies grown on solid atrazine medium (after 10 days of incubation at 30° C.) confirmed the presence of several macromorphologically different colony types in the culture; most often four colony types were present. Clear zones were observed around some of the colonies, which indicated the presence of atrazine-degrading bacteria.

Further characterization of the mixed culture Atz Mix 1 was performed by screening for the genes that are responsible for atrazine degradation using polymerase chain reaction (PCR) method. The PCR program used for amplification was as described in Rousseaux S, Hartmann A and Soulas G 2001 FEMS Microb. Ecol. 36: 211-222; here is given only a short description: total genomic DNA was isolated from the culture Atz Mix 1 grown in shake culture, in the medium containing 1 g $l^{-1}$ of atrazine (optical density, $OD_{600}$=O.4) using a proteinase K protocol according to the manufacturer's instructions (Boehringer Mannheim, Germany). The isolated DNA was used as a template (2.5 μl) in PCR reaction (reaction volume 25 μl) with the primers specific for atrazine-degrading gene amplifications. PCR products were then separated by electrophoresis in 1% agaroze gel, stained with ethydium bromide and photographed under the UV-light by using a digital camera (Canon, Japan).

Molecular characterization of the culture Atz Mix 1 showed the presence of catabolic genes trzN, atzB and atzC coding the enzymes for the transformation of atrazine to cyanuric acid as well as the gene trzD coding the enzymes for the opening of s-triazine ring. Detection of these genes also suggested that atrazine catabolism started with dechlorination (formation of hydroxyatrazine) and was followed by hydrolytical removal of atrazine side-chains (formation of cyanuric acid) and the subsequent cleavage of s-triazine ring. This atrazine catabolic pathway was supported by numerous further experiments in which hydroxyatrazine and cyanuric acid were detected as the main metabolites formed during batch cultivation of the culture Atz Mix 1 under various conditions (see Examples 2 and 3). Furthermore, results of mineralization experiments with the culture Atz Mix 1 using ring labelled [$^{14}C$] atrazine (method described in Rousseaux S, Hartmann A and Soulas G FEMS Microb. Ecol. 2001 36: 211-222) confirmed high degree of atrazine degradation (78%) to the ultimate products $CO_2$ and $NH_4^+$ (see FIG. 1).

Figure 2:
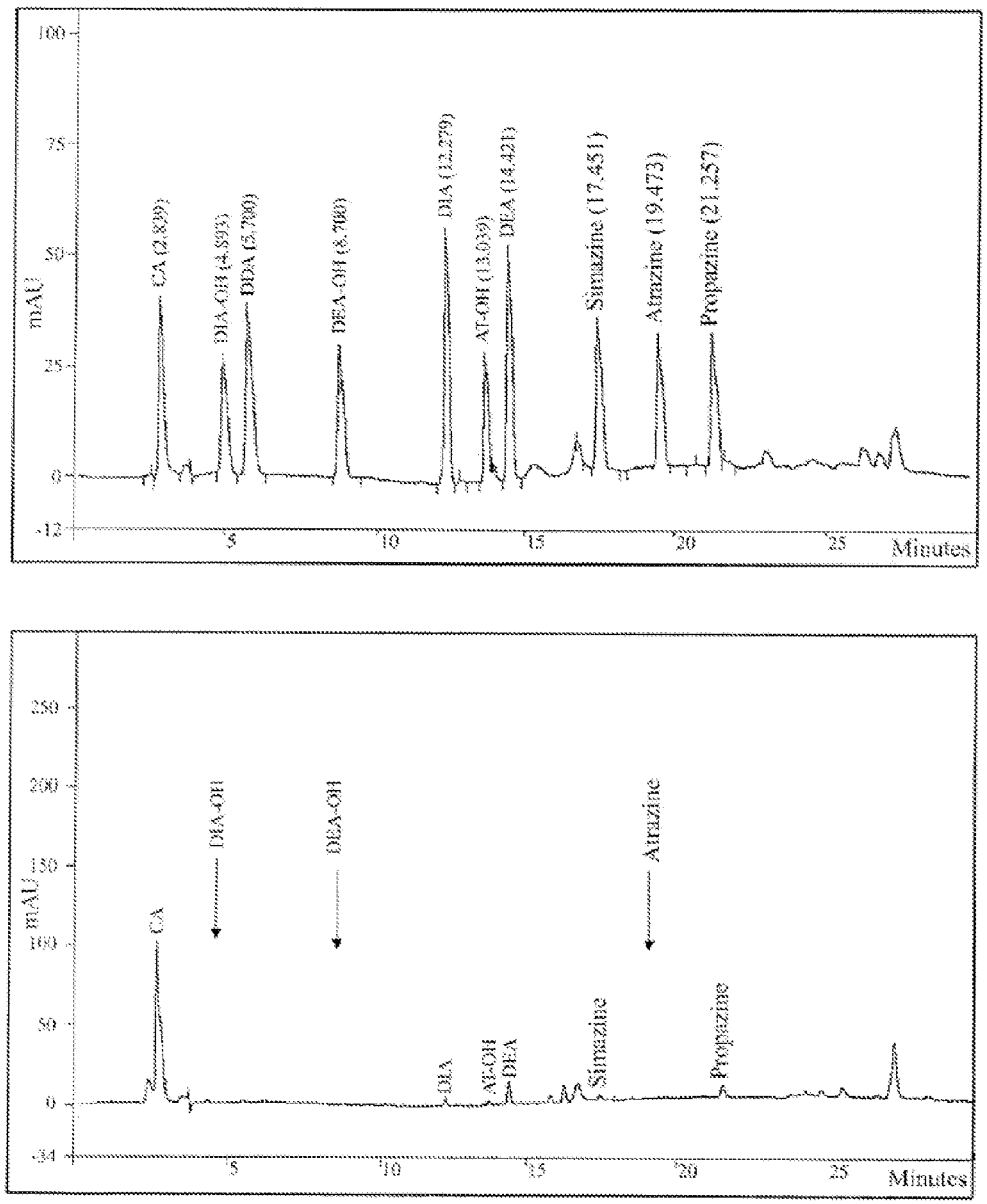
FIG. 2. HPLC-DAD (213 nm) chromatograms at the beginning and after 7-day cultivation of the culture Atz Mix 1 in the medium containing different s-triazine compounds: CA cyanuric acid; DIA-OH hydroxydeisopropylatrazine; DDA deethyldeisopropylatrazine; DEA-OH hydroxydeethylatrazine; DIA deisopropyl-atrazine; AT-OH hydroxyatrazine and DEA deethylatrazine.

To check the activity of the culture Atz Mix 1 in the degradation of other s-triazine compounds, the shake culture method as described in Example 2 was used (the initial concentrations of individual compounds were approximately 2 mg $l^{-1}$) and the experiments were performed at a temperature of 30° C. EDPLC method was used for quantitative determination of the initial and the residual concentrations of individual s-triazine compounds. The chromatograms presented in FIG. 2 suggested that, after 7 days, all examined s-triazine compounds almost completely disappeared except the cyanuric acid, which was detected at a concentration of approximately 1 mg $l^{-1}$. It should be noted that cyanuric acid is a central degradation intermediate for all s-triazine compounds. Consequently, the obtained results suggest that the culture Atz Mix 1 expresses the capability to substantially degrade all tested s-triazine compounds.

EXAMPLE 2

Catabolic Activity of Culture Atz Mix 1 at Different Temperatures

The effect of temperature on the growth of the culture Atz Mix 1 and its catabolic activity was monitored during cultivation in the medium containing the same mineral salts as described in Example $I_5$ with the addition of atrazine (100 mg $l^{-1}$), and sodium citrate (1 g $l^{-1}$) as a carbon source. Experiments were performed in Erlenmeyer flasks (500 ml, 200 ml of medium) with shaking on rotary shaker (200 rev $min^{-1}$) at the temperatures of 10° C., 20° C. and 30° C., respectively. During the experiments, culture growth was monitored by measuring optical density ($OD_{600}$) and the obtained data were converted to biomass dry weight by using calibration curves generated on a dry weight of the culture of known density. Atrazine and the formed intermediates were determined in the culture samples after centrifugation (6000 g, 5 min) by HPLC method. Basic kinetic parameters, specific growth rate of the culture Atz Mix 1 (μ) and specific rate of atrazine degradation (Q), were calculated from the following equations:

$$\mu = 2(X2-X1)/(X2+X1) 1/(t2-t1)$$

where X1 and X2 are biomass concentrations (expressed as dry weight (g $l^{-1}$) at the beginning ($t_1$) and after the specific time ($t_2$) expressed in hours (h)

$$Q = 2(S_1-S_2)/(X_2-+X_1)1/(t_2-t_1)$$

where $S_1$ and $S_2$ are the initial and the residual atrazine concentrations (expressed in mM) at the time $t_1$ and the time $t_2$, respectively.

Figure 3:
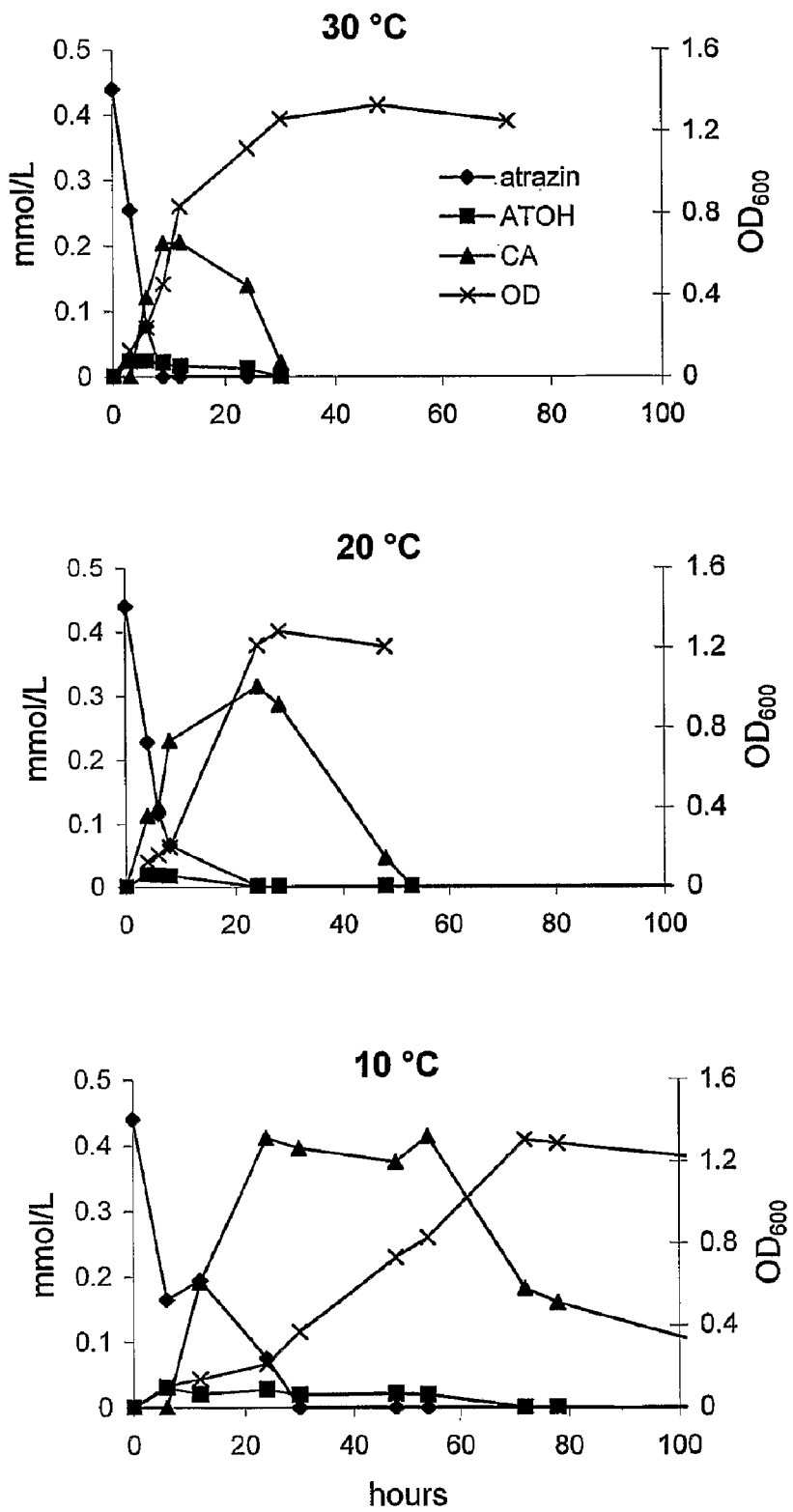
FIG. 3. Growth of the culture Atz Mix 1 (determined as optical density at 600 nm) and atrazine degradation with quantitative analysis of degrading intermediates (by HPLC method) at different temperatures.
Figure 4:
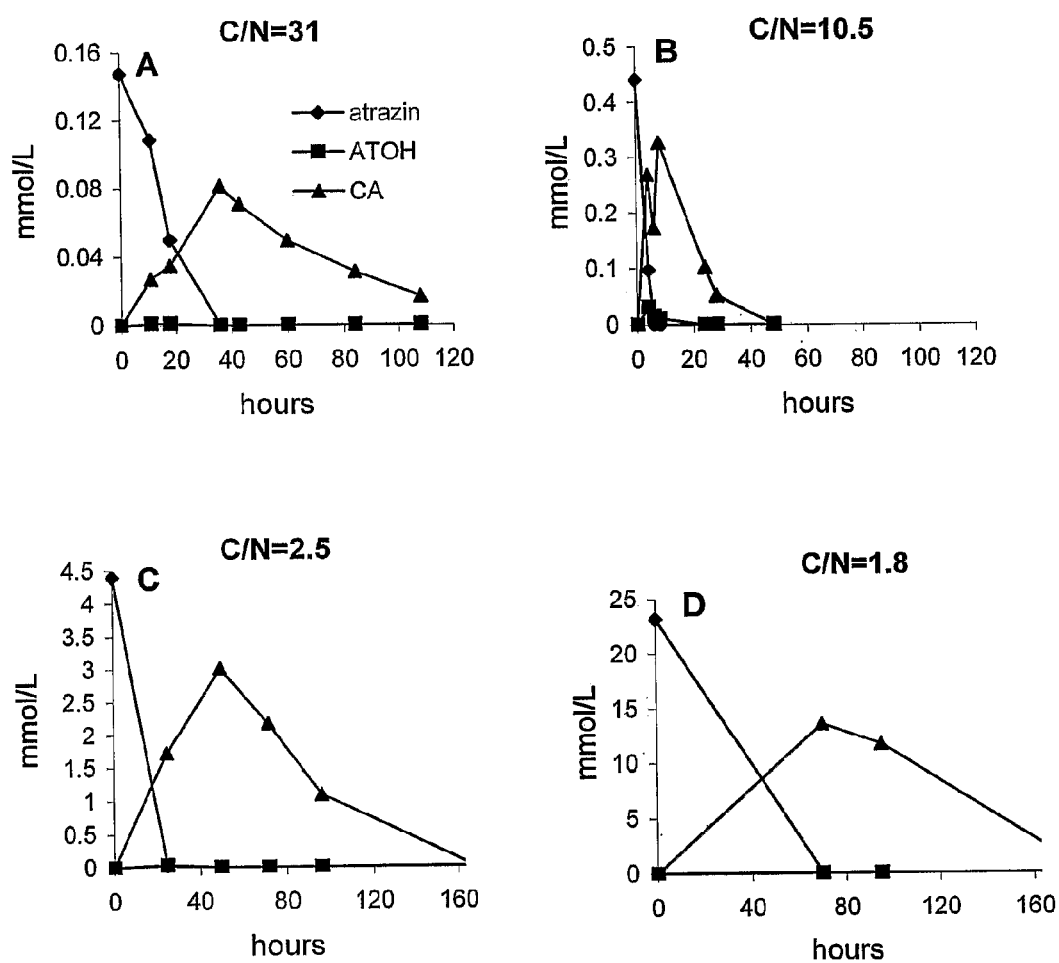
FIG. 4. Atrazine degradation with quantitative analysis of degrading intermediates (by HPLC method) during cultivation of the culture Atz Mix 1 in the medium containing different concentrations of atrazine (30 mg $l^{-1}$-5000 mg $l^{-1}$) as the sole nitrogen source and sodium citrate (1 g $l^{-1}$) as the carbon source (FIG. 4A C/N=31.

When comparing the growth curves of the culture Atz Mix 1 presented in FIG. 3 it is evident that similar culture growth was achieved at 30° C. and 20° C. while with decreasing the temperature to 10° C. the culture growth was significantly slower. However, although slower than at higher temperatures, the same final biomass concentration was yielded at 10°

C., suggesting that the culture Atz Mix 1 possessed the mechanisms for adapting to lower temperatures. Furthermore, although the curves of atrazine disappearance presented in FIG. 3 suggested that the culture Atz Mix 1 was more efficient in atrazine degradation at higher temperatures, the culture still exhibited its specific catabolic activity at 10° C. (i.e. atrazine degradation proceeded through the same metabolic pathway). The analysis of the kinetic parameter, maximum specific rate of atrazine degradation (Table 1), further illustrated that the culture Atz Mix 1 retained significant atrazine degrading activity even at low temperatures (e.g. 10° C.). All afore-mentioned results suggest that the culture Atz Mix 1 might possess the mechanisms for inducing atrazine catabolism under various and varying temperature conditions, most probably owing to the mutual interactions between the culture members, pointing at the same time to the high potential of this culture as a biological agent for accelerating biotransformation processes in atrazine-contaminated environment.

TABLE 1

Kinetics of the culture Atz Mix 1 growth and atrazine degradation at different temperatures

| °C. | $\mu_{max}$ $h^{-1}$ | $Q_{max}$ mM $g^{-1}$ $h^{-1}$ |
|---|---|---|
| 30 | 0.25 ± 0.05 | 1.5 ± 0.05 |
| 20 | 0.12 ± 0.06 | 1.1 ± 0.05 |
| 10 | 0.05 ± 0.04 | 0.5 ± 0.09 |

$\mu_{max}$ is maximum specific growth rate of the culture Atz Mix 1 under experimental conditions $Q_{max}$ is maximum specific rate of atrazine degradation (mM of atrazine per hour per gram of biomass dry weight) under experimental conditions

EXAMPLE 3

Growth and Catabolic Activity of Culture Atz Mix 1 at Different Atrazine Concentrations These investigations were performed during cultivation of the culture Atz Mix 1 in shake flasks at a temperature of 30° C. using AMS medium with the addition of constant amount of sodium citrate (1 g $l^{-1}$) and different amounts of atrazine (initial atrazine concentrations ranging from 30 mg $l^{-1}$ to 10 g $l^{-1}$). Other experimental conditions were the same as described in Example 2.

HPLC analysis of the culture samples during the experiments showed substantial atrazine-degrading activity of the culture Atz Mix 1 in a wide range of atrazine concentrations (FIGS. 4A through 4D). This especially relates to the first step of atrazine degradation (to cyanuric acid). Furthermore, the analysis of kinetic parameters, expressed as maximum specific growth rate and maximum specific rate of atrazine degradation (Table 2), showed that the fastest growth of the culture Atz.

Mix 1 was achieved at the initial atrazine concentrations of 30 mg $l^{-1}$ and 100 mg $l^{-1}$ (molar ratio of carbon and nitrogen, C/N=31.1 and C/N=10.4) while with further increase of atrazine concentration without increasing of carbon source (sodium citrate) culture growth rate gradually decreased. In contrast, specific rate of atrazine degradation increased with increasing the concentration of atrazine to 1000 mg $l^{-1}$ (C/N=2.5) and substantial culture degrading capacity was also expressed at 5000 mg $l^{-1}$ (C/N=1.8). The kinetic parameters presented in Table 2 also suggested that the culture Atz Mix 1 exhibited significant atrazine-degrading activity, i.e. approximately one third of maximum specific rate of atrazine degradation, even at a concentration of 10 g $l^{-1}$.

TABLE 2

Kinetics of the culture Atz Mix 1 growth and atrazine degradation at various initial atrazine concentrations

| Atrazine mg $l^{-1}$ | C/N | $K_{average}$ mg $l^{-1}$ $h^{-1}$ | $\mu_{max}$ $h^{-1}$ | $Q_{max}$ mM $g^{-1}$ $h^{-1}$ |
|---|---|---|---|---|
| 30 | 31.1 | 1.2 ± 0.2 | 0.26 ± 0.05 | 0.6 ± 0.05 |
| 100 | 10.4 | 16.6 ± 1.5 | 0.25 ± 0.04 | 1.5 ± 0.05 |
| 1000 | 2.5 | 39.8 ± 2.5 | 0.14 ± 0.03 | 1.28 ± 0.04 |
| 5000 | 1.8 | 71.4 ± 3.8 | 0.10 ± 0.03 | 1.4 ± 0.05 |
| 10000 | 1.7 | 59.5 ± 5.5 | 0.03 ± 0.02 | 0.5 ± 0.02 |

$K_{average}$ is average atrazine degradation rate under experimental conditions $\mu_{max}$ is maximum specific growth rate of the culture Atz Mix 1 under experimental conditions $Q_{max}$ is maximum specific rate of atrazine degradation (mM of atrazine per hour per gram of biomass dry weight) under experimental conditions

EXAMPLE 4

Growth and Catabolic Activity of Culture Atz Mix 1 in the Presence of Other Nitrogen Sources To evaluate the influence of additional nitrogen sources on catabolic activity of the culture Atz Mix 1, comparative shake-flask experiments were performed using AMS medium with atrazine as the sole nitrogen source (100 mg $l^{-1}$) and with the addition of other nitrogen compounds (urea, $(NH_4)_2SO_4$, $KNO_3$) in the equimolar amount of nitrogen to atrazine (2.3 mM). Other experimental conditions were the same as described in Example 3.

Figure 5:
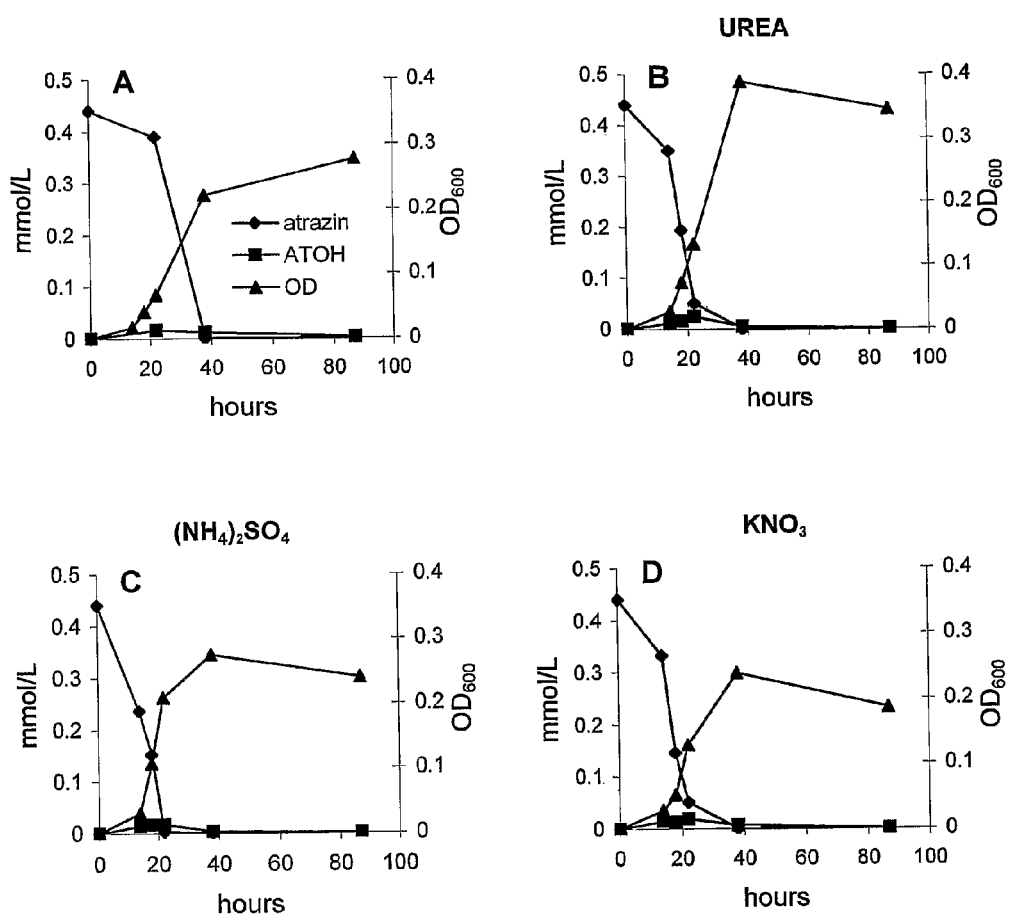
FIG. 5. Growth of the culture Atz Mix 1 and atrazine degradation (determined by HPLC method) during cultivation in the medium with atrazine (100 mg $l^{-1}$) as the sole nitrogen source (FIG. 5A) and in the same medium with the addition of different nitrogen compounds (2.3 niM): urea (FIG. 5B); $(NH_4)_2SO_4$ (FIG. 5C) and $KNO_3$ (FIG. 5D).

The culture growth curves and the curves of atrazine disappearance presented in FIG. 5, suggested that the culture Atz Mix 1 exhibited maximum growth with urea as a supplemental nitrogen source (FIG. 5B) and that the rate of atrazine degradation was higher in the presence of all tested nitrogen sources (FIGS. 5B through 5D) than in the case when atrazine was the sole nitrogen source (FIG. 5A). This further suggested that the culture Atz Mix 1 might possess the mechanisms to overcome the suppressive effect of additional organic or inorganic nitrogen compounds on atrazine catabolism which was observed with the majority of atrazine-degrading bacteria investigated so far. Accordingly, it can be expected that the culture Atz Mix 1 will demonstrate catabolic activity under the conditions when some readily accessible nitrogen sources are present, which is frequently the case in pesticide-contaminated soils and manufacturing waste water.

What is claimed is:

1. A mixed bacterial culture of natural origin which can degrade atrazine and other s-triazine compounds in a range from several ppb to ten thousand ppm at temperatures from 10° C. to 30° C., and which is the culture Atz Mix 1 NCAIM (P) B 001329 2005-12-09 deposited in the National Collection of Agricultural and Industrial Microorganisms, Budapest, Hungary.

2. A culture according to claim 1 which is in the form of a liquid culture, dry culture biomass or culture attached to a support.

3. A culture according to claim 1 wherein said atrazine and other s-triazine compounds comprise one of or a mixture of two or more of atrazine, simazine, propazine, terbutilazine, deethylatrazine, deisopropylatrazine, hydroxyatrazine, hydroxydeisopropylatrazine, hydroxydeethylatrazine, hydroxydeethyldeisopropylatrazine or cyanuric acid.

4. The use of a mixed bacterial culture of natural origin which can degrade atrazine and other s-triazine compounds in a range from several ppb to ten thousand ppm at temperatures from 10° C. to 30° C., and which is the culture Atz Mix 1 NCAIM (P) B 001329 2005-12-09 deposited in the National Collection of Agricultural and Industrial Microorganisms, Budapest, Hungary for remediation of contaminated soil, surface and ground waters or for treatment of waste waters.

5. A use according to claim 4 wherein said atrazine and other s-triazine compounds comprise one of or a mixture of two or more of atrazine, simazine, propazine, terbutilazine, deethylatrazine, deisopropylatrazine, hydroxyatrazine, hydroxydeisopropylatrazine, hydroxydeethylatrazine, hydroxydeethyldeisopropylatrazine or cyanuric acid.

6. A method for degradation of atrazine and other s-triazine compounds comprising subjecting said compounds to the action of a mixed bacterial culture of natural origin which can degrade atrazine and other s-triazine compounds in a range from several ppb to ten thousand ppm at temperatures from 10° C. to 30° C., and which is the culture Atz Mix 1 NCAIM (P) B 001329 2005-12-09 deposited in the National Collection of Agricultural and Industrial Microorganisms, Budapest, Hungary.

7. A method according to claim 6 wherein said atrazine and other s-triazine compounds comprise one of or a mixture of two or more of atrazine, simazine, propazine, terbutilazine, deethylatrazine, deisopropylatrazine, hydroxyatrazine, hydroxydeisopropylatrazine, hydroxydeethylatrazine, hydroxydeethyldeisopropylatrazine or cyanuric acid.

8. A method for degradation of atrazine and other s-triazine compounds in the soil, surface and ground waters or waste waters contaminated by s-triazine compounds, comprising adding a mixed bacterial culture of natural origin which can degrade atrazine and other s-triazine compounds in a range from several ppb to ten thousand ppm at temperatures from 10° C. to 30° C., and which is the culture Atz Mix 1 NCAIM (P) B 001329 2005-12-09 deposited in the National Collection of Agricultural and Industrial Microorganisms, Budapest, Hungary to the soil, surface and ground waters or waste waters.

9. A method according to claim 8 further comprising the step of cultivation of said culture to obtain a sufficient amount of the culture required to obtain a desired degradation of atrazine and other s-triazine compounds in the soil, surface and ground waters or waste waters.

10. A method according to claim 9 characterized in that the cultivation is conducted in batch culture under conditions sufficient to obtain a sufficient amount of the culture.

11. A method according to claim 9 wherein the culture is cultivated in a mineral medium containing atrazine as the carbon and nitrogen source and as the inducer of degrading enzymes, with the addition of a supplemental carbon source and specific nutrients.

12. A method according to claim 9 wherein a mineral component of the medium comprises potassium salts, magnesium salt, zinc salt, iron salt, manganese salt or copper salt in the form of phosphate or sulphate, the supplemental carbon source is sodium citrate and the source of specific nutrients is yeast extract.

13. A method according to claim 8 wherein said atrazine and other s-triazine compounds comprise one of or a mixture of two or more of atrazine, simazine, propazine, terbutilazine, deethylatrazine, deisopropylatrazine, hydroxyatrazine, hydroxydeisopropylatrazine, hydroxydeethylatrazine, hydroxydeethyldeisopropylatrazine or cyanuric acid.

14. A method for degradation of atrazine and other s-triazine compounds in waste waters containing high concentration of atrazine and other s-triazine compounds, comprising the steps of inoculating a mixed bacterial culture of natural origin which can degrade atrazine and other s-triazine compounds in a range from several ppb to ten thousand ppm at temperatures from 10° C. to 30° C., and which is the culture Atz Mix 1 NCAIM (P) B 001329 2005-12-09 deposited in the National Collection of Agricultural and Industrial Microorganisms, Budapest, Hungary, adding a supplemental carbon source, specific nutrients or mineral salts to the waste water and then culturing said inoculated culture.

15. A method according to claim 14 wherein the supplemental carbon source is sodium citrate, the source of specific nutrients is yeast extract and mineral salts are selected from potassium salts, magnesium salt, zinc salt, iron salt, manganese salt or copper salt in the form of phosphate or sulphate.

16. A method according to claim 14 wherein said atrazine and other s-triazine compounds comprise one of or a mixture of two or more of atrazine, simazine, propazine, terbutilazine, deethylatrazine, deisopropylatrazine, hydroxyatrazine, hydroxydeisopropylatrazine, hydroxydeethylatrazine, hydroxydeethyldeisopropylatrazine or cyanuric acid.

* * * * *